US010786277B2

(12) United States Patent
Ranallo et al.

(10) Patent No.: US 10,786,277 B2
(45) Date of Patent: Sep. 29, 2020

(54) RETRIEVAL DEVICE

(71) Applicant: UNITED STATES ENDOSCOPY GROUP, INC., Mentor, OH (US)

(72) Inventors: Cynthia Ann Ranallo, Eastlake, OH (US); Alex Uspenski, Chardon, OH (US); Joseph Michelini, Painesville, OH (US); Christopher Kaye, Eastlake, OH (US); Scott Haack, Moreland Hills, OH (US)

(73) Assignee: UNITED STATE ENDOSCOPY GROUP, INC., Mentor, OH (US)

( * ) Notice: Subject to any disclaimer, the term of this patent is extended or adjusted under 35 U.S.C. 154(b) by 236 days.

(21) Appl. No.: 15/866,273

(22) Filed: Jan. 9, 2018

(65) Prior Publication Data
US 2018/0193009 A1 Jul. 12, 2018

Related U.S. Application Data

(60) Provisional application No. 62/444,144, filed on Jan. 9, 2017.

(51) Int. Cl.
*A61B 17/3205* (2006.01)
*A61B 17/00* (2006.01)
(Continued)

(52) U.S. Cl.
CPC .. *A61B 17/32056* (2013.01); *A61B 17/00234* (2013.01); *A61B 17/221* (2013.01);
(Continued)

(58) Field of Classification Search
CPC . A61B 90/92; A61B 17/221; A61B 17/00234; A61B 17/320016;
(Continued)

(56) References Cited

U.S. PATENT DOCUMENTS 640,940 A 10/1891 Baughli
2,197,921 A 4/1940 Brown
(Continued)

FOREIGN PATENT DOCUMENTS

DE 19938902 A1 4/2000
EP 0446020 A1 9/1991
(Continued)

OTHER PUBLICATIONS

Response to Office Action from U.S. Appl. No. 14/875,028 dated Mar. 26, 2019.
(Continued)

*Primary Examiner* — Phong Son H Dang

(74) *Attorney, Agent, or Firm* — Calfee, Halter & Griswold LLP

(57) ABSTRACT

The present subject matter provides improvements of endoscopic retrieving devices. In specific, the present subject matter provides a net element with an extra wide tail section. The present subject matter provides a new weaving pattern. The present subject matter provides a new shape of the loop. The present subject matter provides a net with a combination of net elements, such as combinations of different net geometries and/or different net materials. The present subject matter provides a new and inventive loop. The present subject matter provides an improved second end of the tubular member. The present subject matter provides a new and inventive arm.

23 Claims, 12 Drawing Sheets

(51) Int. Cl.
*A61B 90/92* (2016.01)
*A61B 17/221* (2006.01)
*A61B 17/32* (2006.01)

(52) U.S. Cl.
CPC ...... *A61B 17/320016* (2013.01); *A61B 90/92* (2016.02); *A61B 2017/00358* (2013.01); *A61B 2017/00367* (2013.01); *A61B 2017/00438* (2013.01); *A61B 2017/2212* (2013.01); *A61B 2017/2217* (2013.01)

(58) Field of Classification Search
CPC .... A61B 17/32056; A61B 2017/00438; A61B 2017/2217; A61B 2017/00358; A61B 2017/00367; A61B 2017/2212
See application file for complete search history.

(56) References Cited

U.S. PATENT DOCUMENTS

| | | |
|---|---|---|
| 2,626,447 A | 1/1953 | Hunt |
| 3,805,791 A | 4/1974 | Seuberth et al. |
| 4,083,706 A | 4/1978 | Wiley |
| 4,146,019 A | 3/1979 | Bass et al. |
| 4,200,104 A | 4/1980 | Harris |
| 4,202,338 A | 5/1980 | Bitrolf |
| 4,256,113 A | 3/1981 | Chamness |
| 4,311,143 A | 1/1982 | Komlya |
| 4,493,320 A | 1/1985 | Treat |
| 4,905,691 A | 3/1990 | Rydell |
| 4,966,589 A | 10/1990 | Kaufman |
| 5,009,642 A | 4/1991 | Sahi |
| 5,057,114 A | 10/1991 | Wittich et al. |
| 5,059,199 A | 10/1991 | Okada et al. |
| 5,078,716 A * | 1/1992 | Doll ............ A61B 18/14 606/47 |
| 5,084,054 A | 1/1992 | Bencini et al. |
| 5,098,441 A | 3/1992 | Wechler |
| 5,122,147 A * | 6/1992 | Sewell, Jr. ....... A61B 17/32056 606/110 |
| 5,123,906 A | 6/1992 | Kelman |
| 5,147,371 A | 9/1992 | Washington |
| 5,156,590 A | 10/1992 | Vilmar |
| 5,171,233 A | 12/1992 | Amplatz et al. |
| 5,190,542 A | 3/1993 | Nakao |
| 5,192,280 A | 3/1993 | Parins |
| 5,192,286 A | 3/1993 | Phan et al. |
| 5,201,740 A | 4/1993 | Nakao et al. |
| 5,207,686 A | 5/1993 | Dolgin |
| 5,279,548 A | 1/1994 | Essig et al. |
| 5,336,227 A | 8/1994 | Nakao et al. |
| 5,354,303 A | 10/1994 | Spaeth et al. |
| 5,373,854 A | 12/1994 | Kolozsi |
| 5,374,273 A | 12/1994 | Nakao et al. |
| 5,376,094 A | 12/1994 | Kline |
| 5,417,697 A | 5/1995 | Wilk et al. |
| 5,423,830 A | 6/1995 | Schneebaum et al. |
| 5,441,503 A | 8/1995 | Considine et al. |
| 5,449,372 A | 9/1995 | Schmaitz et al. |
| 5,480,404 A | 1/1996 | Kammerer et al. |
| 5,496,330 A | 3/1996 | Bates et al. |
| 5,501,692 A | 3/1996 | Riza |
| 5,536,248 A | 7/1996 | Weaver et al. |
| 5,542,948 A | 8/1996 | Weaver et al. |
| 5,599,299 A | 2/1997 | Weaver et al. |
| 5,599,300 A | 2/1997 | Weaver et al. |
| 5,643,283 A | 7/1997 | Younker |
| 5,666,970 A | 9/1997 | Smith |
| 5,741,271 A | 4/1998 | Nakao et al. |
| 5,759,187 A * | 6/1998 | Nakao ............ A61B 1/015 606/110 |
| 5,779,686 A | 7/1998 | Sato et al. |
| 5,782,840 A * | 7/1998 | Nakao ............ A61B 18/14 606/110 |
| 5,785,689 A | 7/1998 | de Toledo |
| 5,788,681 A | 8/1998 | Weaver et al. |
| 5,810,776 A | 9/1998 | Bacich et al. |
| 5,843,028 A | 12/1998 | Weaver et al. |
| 5,843,051 A | 12/1998 | Adams et al. |
| 5,846,248 A | 12/1998 | Chu et al. |
| 5,860,987 A | 1/1999 | Ratcliff et al. |
| 5,906,594 A | 5/1999 | Scarfone et al. |
| 5,906,621 A | 5/1999 | Secrest et al. |
| 5,947,979 A | 9/1999 | Ouchi et al. |
| 5,961,526 A | 10/1999 | Chu et al. |
| 5,964,740 A | 10/1999 | Ouchi et al. |
| 5,971,994 A | 10/1999 | Fritzsch |
| 5,971,995 A | 10/1999 | Rousseau |
| 5,976,073 A | 11/1999 | Ouchi |
| 5,989,264 A | 11/1999 | Wright |
| 5,997,547 A | 12/1999 | Nakao et al. |
| 6,007,546 A | 12/1999 | Snow et al. |
| 6,010,512 A | 1/2000 | Chu et al. |
| 6,015,391 A | 1/2000 | Rishton et al. |
| 6,015,415 A | 1/2000 | Avellanet |
| 6,050,995 A | 4/2000 | Durgin |
| 6,068,603 A | 5/2000 | Suzuki |
| 6,093,195 A | 7/2000 | Ouchi |
| 6,123,665 A | 9/2000 | Kawano |
| 6,142,956 A | 11/2000 | Kortenbach et al. |
| 6,171,315 B1 | 1/2001 | Chu et al. |
| 6,174,291 B1 | 1/2001 | McMahon et al. |
| 6,183,482 B1 | 2/2001 | Bates et al. |
| 6,190,353 B1 | 2/2001 | Makower et al. |
| 6,193,672 B1 | 2/2001 | Clement |
| 6,210,416 B1 | 4/2001 | Chu et al. |
| 6,224,611 B1 | 5/2001 | Ouchi |
| 6,235,026 B1 | 5/2001 | Smith |
| 6,245,078 B1 | 6/2001 | Ouchi |
| 6,264,664 B1 | 7/2001 | Avellanet |
| 6,299,612 B1 | 10/2001 | Ouchi |
| 6,315,782 B1 | 11/2001 | Chu et al. |
| 6,319,260 B1 | 11/2001 | Yamamoto |
| 6,352,503 B1 | 3/2002 | Matsui et al. |
| 6,375,661 B2 | 4/2002 | Chu et al. |
| 6,383,194 B1 | 5/2002 | Pothula |
| 6,383,198 B1 | 5/2002 | Hamilton |
| 6,407,333 B1 | 6/2002 | Schroen |
| 6,409,733 B1 | 6/2002 | Conlon et al. |
| 6,440,138 B1 | 8/2002 | Reiley et al. |
| 6,458,074 B1 | 10/2002 | Matsui et al. |
| 6,500,182 B2 | 12/2002 | Foster |
| 6,517,551 B1 | 2/2003 | Driskill |
| 6,527,753 B2 | 3/2003 | Sekine et al. |
| 6,527,781 B2 | 3/2003 | Bates et al. |
| 6,602,262 B2 | 8/2003 | Griego et al. |
| 6,616,654 B2 | 9/2003 | Mclennauer |
| 6,616,659 B1 | 9/2003 | de la Torre et al. |
| 6,669,716 B1 | 12/2003 | Gilson et al. |
| 6,685,722 B1 | 2/2004 | Rosenbluth et al. |
| 6,730,097 B2 | 5/2004 | Dennis |
| 6,743,228 B2 | 6/2004 | Lee et al. |
| 6,770,066 B1 | 8/2004 | Weaver et al. |
| 6,773,432 B1 | 8/2004 | Clayman et al. |
| 6,814,739 B2 | 11/2004 | Secrest |
| 6,827,710 B1 | 12/2004 | Money et al. |
| 6,945,956 B2 | 9/2005 | Waldhauser et al. |
| 7,001,354 B2 | 2/2006 | Suzuki et al. |
| 7,037,291 B2 | 5/2006 | Lee et al. |
| 7,037,307 B2 | 5/2006 | Dennis |
| 7,041,116 B2 | 5/2006 | Goto et al. |
| 7,044,947 B2 | 5/2006 | de la Torre et al. |
| 7,104,990 B2 | 9/2006 | Jenkins et al. |
| 7,122,003 B2 | 10/2006 | Nakao |
| 7,147,635 B2 | 12/2006 | Ciarrocca |
| 7,270,663 B2 | 9/2007 | Nakao |
| 7,387,632 B2 | 6/2008 | Ouchi |
| 7,547,310 B2 | 6/2009 | Whitfield |
| 7,575,585 B2 | 8/2009 | Goto et al. |
| 7,632,294 B2 | 12/2009 | Milbodker et al. |
| 7,691,110 B2 | 4/2010 | Secrest et al. |
| 7,704,249 B2 | 4/2010 | Woloszko et al. |
| 7,758,591 B2 | 7/2010 | Griego et al. |
| 7,785,250 B2 | 8/2010 | Nakao |

(56) References Cited

U.S. PATENT DOCUMENTS

| | | |
|---|---|---|
| 7,951,073 B2 | 5/2011 | Freed |
| 7,972,265 B1 | 7/2011 | Chin et al. |
| 8,016,838 B2* | 9/2011 | Kaye ................. A61B 17/221 |
| | | 606/113 |
| 8,057,484 B2 | 11/2011 | Secrest |
| 8,066,689 B2 | 11/2011 | Mitelberg et al. |
| 8,070,756 B2 | 12/2011 | Secrest |
| 8,075,572 B2 | 12/2011 | Stefanchik et al. |
| 8,100,905 B2 | 1/2012 | Weitzner |
| 8,114,099 B2 | 2/2012 | Shipp |
| 8,128,592 B2 | 3/2012 | Mitelberg et al. |
| 8,167,893 B2 | 5/2012 | Motosugi |
| 8,187,266 B2 | 5/2012 | Dickens et al. |
| 8,216,272 B2 | 7/2012 | Shipp |
| 8,241,210 B2 | 8/2012 | Lunsford et al. |
| 8,267,933 B2 | 9/2012 | Hamou |
| 8,282,658 B2 | 10/2012 | Knapp et al. |
| 8,298,243 B2 | 10/2012 | Carlton et al. |
| 8,317,771 B2 | 11/2012 | Mitelberg et al. |
| 8,328,803 B2 | 12/2012 | Regadas |
| 8,343,168 B2 | 1/2013 | Kaye et al. |
| 8,357,148 B2 | 1/2013 | Boulais et al. |
| 8,366,612 B2 | 2/2013 | Rosenthal |
| 8,372,066 B2 | 2/2013 | Manwaring et al. |
| 8,388,630 B2 | 3/2013 | Teague et al. |
| 8,591,521 B2 | 11/2013 | Cherry et al. |
| 9,486,188 B2 | 11/2016 | Secrest et al. |
| 9,572,591 B2 | 2/2017 | Haack |
| 9,730,716 B2 | 8/2017 | Secrest |
| 9,872,700 B2 | 1/2018 | Haack |
| 2002/0049423 A1 | 4/2002 | Howell et al. |
| 2002/0091394 A1 | 7/2002 | Reynolds et al. |
| 2002/0151889 A1 | 10/2002 | Swanson et al. |
| 2003/0004538 A1* | 1/2003 | Secrest ............ A61B 17/00234 |
| | | 606/200 |
| 2003/0139750 A1* | 7/2003 | Shinozuka ........... A61B 17/221 |
| | | 606/113 |
| 2003/0195470 A1 | 10/2003 | Ponzi |
| 2003/0195492 A1 | 10/2003 | Gobron et al. |
| 2003/0216753 A1 | 11/2003 | Nishtala et al. |
| 2003/0236519 A1 | 12/2003 | Kear |
| 2004/0059352 A1 | 3/2004 | Burbank et al. |
| 2004/0092953 A1* | 5/2004 | Salameh .......... A61B 17/32056 |
| | | 606/113 |
| 2004/0158127 A1 | 8/2004 | Okada |
| 2005/0043743 A1 | 2/2005 | Dennis |
| 2005/0085808 A1 | 4/2005 | Nakao |
| 2005/0107668 A1 | 5/2005 | Smith |
| 2005/0165412 A1 | 7/2005 | Secrest et al. |
| 2005/0267489 A1* | 12/2005 | Secrest .................. A61B 17/22 |
| | | 606/113 |
| 2005/0267490 A1 | 12/2005 | Secrest et al. |
| 2006/0009759 A1 | 1/2006 | Christian et al. |
| 2006/0058776 A1 | 3/2006 | Bilsbury |
| 2006/0229640 A1* | 10/2006 | Whitfield ............. A61B 17/221 |
| | | 606/114 |
| 2006/0235433 A1 | 10/2006 | Secrest |
| 2006/0247662 A1 | 11/2006 | Schwartz et al. |
| 2006/0264977 A1 | 11/2006 | Dana et al. |
| 2007/0016224 A1 | 1/2007 | Nakao |
| 2007/0016225 A1* | 1/2007 | Nakao ................. A61B 17/221 |
| | | 606/114 |
| 2007/0250070 A1 | 10/2007 | Nobis et al. |
| 2007/0288035 A1 | 12/2007 | Okada |
| 2008/0045945 A1 | 2/2008 | Hamou |
| 2008/0183184 A1 | 7/2008 | Kaye et al. |
| 2008/0306336 A1 | 12/2008 | Kaye |
| 2009/0043317 A1 | 2/2009 | Cavanaugh et al. |
| 2009/0112244 A1 | 4/2009 | Freudenthal |
| 2010/0036375 A1* | 2/2010 | Regadas ................ A61B 18/14 |
| | | 606/39 |
| 2010/0268206 A1 | 10/2010 | Manwaring et al. |
| 2010/0268216 A1 | 10/2010 | Manwaring |
| 2011/0106077 A1 | 5/2011 | Yanuma et al. |
| 2011/0106107 A1 | 5/2011 | Binmoeller et al. |
| 2012/0004666 A1 | 1/2012 | Cowley et al. |
| 2012/0046667 A1* | 2/2012 | Cherry ................. A61B 17/221 |
| | | 606/113 |
| 2012/0172662 A1* | 7/2012 | Kappel ................ A61B 17/221 |
| | | 600/104 |
| 2012/0172864 A1 | 7/2012 | Farin et al. |
| 2012/0184967 A1 | 7/2012 | Saleh |
| 2012/0283723 A1 | 11/2012 | Jenkins et al. |
| 2013/0018384 A1 | 1/2013 | Kappel et al. |
| 2013/0018385 A1 | 1/2013 | Keene et al. |
| 2014/0243885 A1 | 8/2014 | Eckhouse et al. |
| 2014/0276810 A1* | 9/2014 | Raybin ................. A61B 18/14 |
| | | 606/46 |
| 2014/0276911 A1* | 9/2014 | Smith .................. A61B 17/221 |
| | | 606/113 |
| 2015/0105789 A1* | 4/2015 | Raybin ............ A61B 17/32056 |
| | | 606/113 |
| 2015/0157345 A1* | 6/2015 | Haack ................. A61B 17/221 |
| | | 606/113 |
| 2016/0045210 A1 | 2/2016 | Cherry et al. |
| 2016/0242804 A1* | 8/2016 | Fleury .............. A61B 17/32056 |
| 2017/0007277 A1* | 1/2017 | Drapeau ............ A61B 18/1482 |
| 2017/0049471 A1* | 2/2017 | Gaffney ......... A61B 17/320016 |
| 2017/0231647 A1* | 8/2017 | Saunders ............. A61B 17/221 |
| | | 606/113 |
| 2018/0028220 A1* | 2/2018 | Smith .............. A61B 17/32056 |

FOREIGN PATENT DOCUMENTS

| | | |
|---|---|---|
| EP | 463363 A2 | 1/1992 |
| EP | 758551 A1 | 2/1997 |
| EP | 1180349 A1 | 2/2002 |
| EP | 1870015 A1 | 12/2007 |
| JP | 3-54652 | 5/1991 |
| JP | 5-091686 | 4/1993 |
| JP | 3250621 | 8/1993 |
| JP | H06154161 A | 6/1994 |
| JP | H07101802 A | 4/1995 |
| JP | 10-071166 | 3/1998 |
| JP | 10-174688 | 6/1998 |
| JP | 11-047154 | 2/1999 |
| JP | 11-226024 | 8/1999 |
| JP | H11309150 A | 11/1999 |
| JP | 2000-175930 | 6/2000 |
| JP | 2000-210295 | 8/2000 |
| JP | 2000-316868 | 11/2000 |
| JP | 2000-342600 | 12/2000 |
| JP | 2003-052707 | 2/2003 |
| JP | M03-511140 | 3/2003 |
| JP | 2004-532683 A | 10/2004 |
| JP | 2007-534451 | 11/2007 |
| WO | 93/015671 A1 | 8/1993 |
| WO | 99/42041 A1 | 8/1999 |
| WO | 99/51159 A1 | 10/1999 |
| WO | 02/094082 A2 | 11/2002 |
| WO | 03/105674 A2 | 12/2003 |
| WO | 05/115116 A2 | 12/2005 |
| WO | 05/115120 A2 | 12/2005 |
| WO | 2006112231 A1 | 10/2006 |
| WO | 2007000452 A2 | 1/2007 |
| WO | 08/094931 A2 | 8/2008 |
| WO | 08/154406 A1 | 12/2008 |

OTHER PUBLICATIONS

Office Action from U.S. Appl. No. 14/875,028 dated Jul. 1, 2019.
Response to Office Action Office Action from U.S. Appl. No. 15/401,545 dated Jun. 10, 2019.
Office Action from U.S. Appl. No. 15/401,545 dated Jun. 27, 2019.
Response to Office Action Office Action from U.S. Appl. No. 15/401,545 dated Sep. 26, 2019.
Office Action from U.S. Appl. No. 15/676,725 dated Jul. 5, 2019.
Communication Pursuant to Article 94(3) from European Application No. 18167984.6 dated Jun. 6, 2019.
Response to Office Action from U.S. Appl. No. 14/875,028 dated Jun. 19, 2018.

(56) References Cited

OTHER PUBLICATIONS

Office Action from U.S. Appl. No. 14/875,028 dated Aug. 27, 2018.
Response to Office Action from U.S. Appl. No. 14/875,028 dated Nov. 27, 2018.
Office Action from U.S. Appl. No. 15/401,545 dated Aug. 2, 2018.
Response to Office Action from U.S. Appl. No. 15/401,545 dated Oct. 30, 2018.
Communication Pursuant to Article 94(3) EPC from European Application No. 05755966.8 dated Oct. 22, 2018.
Communication Pursuant to Artile 94(3) EPC from European Application No. 12162767.3 dated Nov. 12, 2018.
Extended Search Report from European Application No. 18167984.6 dated Jul. 30, 2018.
International Search Report and Written Opinion from PCT/US02/15465 dated Aug. 26, 2003.
International Preliminary Examination Report from PCT/US02/15465 dated Nov. 12, 2003.
International Search Report from and Written Opinion from PCT/US05/18294 dated Jul. 3, 2007, 6 pgs.
International Search Report and Written Opinion from PCT/US05/18497 dated May 8, 2008.
International Search Report and Written Opinion from PCT/US08/52342 dated Jul. 30, 2008.
International Search Report and Written Opinion from PCT/US08/066161 dated Sep. 22, 2008.
International Search Report and Written Opinion from PCT/US2014/053828 dated Dec. 30, 2014.
International Preliminary Report on Patentability from PCT/US2014/053828 dated Mar. 8, 2016.
International Search Report and Written Opinion from PCT/US18/13017 dated Apr. 6, 2018.
Office Action from U.S. Appl. No. 11/137,814 dated May 16, 2007.
Response from U.S. Appl. No. 11/137,814 dated Aug. 16, 2007.
Office Action from U.S. Appl. No. 11/137,814 dated Dec. 07, 2007.
Response from U.S. Appl. No. 11/137,814 dated Apr. 7, 2008.
Office Action from U.S. Appl. No. 11/137,814 dated Jul. 18, 2008.
Response from U.S. Appl. No. 11/137,814 dated Sep. 18, 2008.
Interview Summary and Advisory Action from U.S. Appl. No. 11/137,814 dated Oct. 14, 2008.
Response from U.S. Appl. No. 11/137,814 dated Nov. 18, 2008.
Office Action from U.S. Appl. No. 11/137,814 dated Feb. 12, 2009.
Response from U.S. Appl. No. 11/137,814 dated Aug. 12, 2009.
Office Action from U.S. Appl. No. 11/137,814 dated Nov. 23, 2009.
Response from U.S. Appl. No. 11/137,814 dated Jan. 19, 2010.
Notice of Allowance from U.S. Appl. No. 11/137,814 dated Feb. 18, 2010.
Office Action from U.S. Appl. No. 11/404,345 dated Jun. 27, 2008.
Interview Summary from U.S. Appl. No. 11/404,345 dated Oct. 7, 2008.
Response from U.S. Appl. No. 11/404,345 dated Nov. 26, 2008.
Office Action from U.S. Appl. No. 11/404,345 dated Mar. 11, 2010.
Response from U.S. Appl. No. 11/404,345 dated May 11, 2010.
Advisory Action from U.S. Appl. No. 11/404,345 dated May 27, 2010.
Response from U.S. Appl. No. 11/404,345 dated Sep. 13, 2010.
Office Action from U.S. Appl. No. 11/404,345 dated Dec. 29, 2010.
Response from U.S. Appl. No. 11/404,345 dated May 25, 2011.
Notice of Allowance from U.S. Appl. No. 11/404,345 dated Aug. 19, 2011.
Office Action from U.S. Appl. No. 12/021,903 dated Dec. 10, 2009.
Response from U.S. Appl. No. 12/021,903 dated Jun. 9, 2010.
Office Action from U.S. Appl. No. 12/021,903 dated Aug. 5, 2010.
Response from U.S. Appl. No. 12/021,903 dated Oct. 7, 2010.
Interview Summary from U.S. Appl. No. 12/021,903 dated Oct. 5, 2010.
Office Action from U.S. Appl. No. 12/021,903 dated Dec. 29, 2011.
Interview Summary from U.S. Appl. No. 12/021,903 date Mar. 21, 2012.
Response from U.S. Appl. No. 12/021,903 dated May 25, 2012.
Notice of Allowance from U.S. Appl. No. 12/021,903 dated Aug. 9, 2012.
Notice of Allowance from U.S. Appl. No. 12/021,903 dated Nov. 20, 2012.
Office Action from U.S. Appl. No. 14/016,906 dated Apr. 8, 2015.
Response to Office Action from U.S. Appl. No. 14/016,906 dated Feb. 12, 2016.
Office Action from U.S. Appl. No. 14/016,906 dated May 31, 2016.
Response to Office Action from U.S. Appl. No. 14/016,906 dated Jul. 28, 2016.
Office Action from U.S. Appl. No. 14/016,906 dated Sep. 13, 2016.
Response to Office Action from U.S. Appl. No. 14/016,906 dated Dec. 13, 2016.
Office Action from U.S. Appl. No. 14/016,906 dated Mar. 10, 2017.
Response to Office Action from U.S. Appl. No. 14/016,906 dated Aug. 10, 2017.
Response from U.S. Appl. No. 10/146,273 dated May 26, 2004.
Notice of Allowance from U.S. Appl. No. 10/146,273 dated Jul. 12, 2004.
Office Action from U.S. Appl. No. 10/965,542 dated Jun. 25, 2008.
Interview Summary from U.S. Appl. No. 10/965,542 dated Oct. 14, 2008.
Response from U.S. Appl. No. 10/965,542 dated Oct. 27, 2008.
Office Action from U.S. Appl. No. 10/965,542 dated Feb. 4, 2009.
Response from U.S. Appl. No. 10/965,542 dated Aug. 4, 2009.
Office Action from U.S. Appl. No. 10/965,542 dated Oct. 14, 2009.
Response from U.S. Appl. No. 10/965,542 dated Apr. 14, 2010.
Office Action from U.S. Appl. No. 10/965,542 dated Jun. 30, 2010.
Response from U.S. Appl. No. 10/965,542 dated Dec. 29, 2010.
Office Action from U.S. Appl. No. 10/965,542 dated May 21, 2013.
Response from U.S. Appl. No. 10/965,542 dated Sep. 23, 2013.
Office Action from U.S. Appl. No. 10/965,542 dated Dec. 27, 2013.
RCE and Response to Office Action from U.S. Appl. No. 10/965,542 dated May 27, 2014.
Office Action from U.S. Appl. No. 10/965,542 dated Aug. 11, 2014.
Interview Summary from U.S. Appl. No. 10/965,542 dated Dec. 17, 2014.
Amendment from U.S. Appl. No. 10/965,542 dated Jan. 12, 2015.
Office Action from U.S. Appl. No. 10/965,542 dated Feb. 20, 2015.
Response to Office Action from U.S. Appl. No. 10/965,542 dated Aug. 20, 2015.
Office Action from U.S. Appl. No. 10/965,542 dated Sep. 18, 2015.
Response to Office Action from U.S. Appl. No. 10/965,542 dated Jan. 19, 2016.
Notice of Allowance from U.S. Appl. No. 10/965,542 dated Jul. 11, 2016.
Office Action from U.S. Appl. No. 11/137,763 dated Jun. 24, 2009.
Supplemental Office Action from U.S. Appl. No. 11/137,763 dated Sep. 9, 2009.
Response from U.S. Appl. No. 11/137,763 dated Mar. 3, 2010.
Office Action from U.S. Appl. No. 11/137,763 dated May 25, 2010.
Response from U.S. Appl. No. 11/137,763 dated Jul. 23, 2010.
Advisory Action from U.S. Appl. No. 11/137,763 dated Aug. 5, 2010.
Office Action from U.S. Appl. No. 11/137,763 dated Dec. 23, 2010.
Interview Summary from U.S. Appl. No. 11/137,763 dated May 12, 2011.
Response from U.S. Appl. No. 11/137,763 dated May 23, 2011.
Office Action from U.S. Appl. No. 11/137,763 dated Aug. 4, 2011.
Response from U.S. Appl. No. 11/137,763 dated Aug. 22, 2011.
Notice of Allowance from U.S. Appl. No. 11/137,763 dated Sep. 19, 2011.
Office action from U.S. Appl. No. 12/135,473 dated Nov. 16, 2010.
Response from U.S. Appl. No. 12/135,473 dated Feb. 15, 2011.
Interview Summary from U.S. Appl. No. 12/135,473 dated Feb. 15, 2011.
Office Communication from U.S. Appl. No. 12/135,473 dated Apr. 15, 2011.
Notice of Allowance from U.S. Appl. No. 12/135,473 dated Jun. 27, 2011.
Office Action from U.S. Appl. No. 13/213,689 dated Dec. 20, 2012.
Response from U.S. Appl. No. 13/213,689 dated Mar. 18, 2013.

(56) References Cited

OTHER PUBLICATIONS

Notice of Allowance from U.S. Appl. No. 13/213,689 dated Jul. 23, 2013.
Office Action from U.S. Appl. No. 14/061,395 dated Jun. 18, 2015.
Response to Office Action from U.S. Appl. No. 14/061,395 dated Sep. 17, 2015.
Office Action from U.S. Appl. No. 14/875,028 dated Jun. 1, 2017.
Response to Office Action from U.S. Appl. No. 14/875,028 dated Sep. 27, 2017.
Office Action from U.S. Appl. No. 14/875,028 dated Oct. 18, 2017.
Response to Office Action from U.S. Appl. No. 14/875,028 dated Jan. 17, 2018.
Office Action from U.S. Appl. No. 14/875,028 dated Mar. 29, 2018.
Notice of Allowance from U.S. Appl. No. 14/016,906 dated Sep. 27, 2017.
Office Action from U.S. Appl. No. 14/565,024 dated Apr. 17, 2015.
Response to Office Action from U.S. Appl. No. 14/565,024 dated Aug. 17, 2015.
Response to Office Action from U.S. Appl. No. 14/565,024 dated Mar. 25, 2016.
Advisory Action from U.S. Appl. No. 14/565,024 dated Apr. 14, 2016.
Office Action from U.S. Appl. No. 14/565,024 dated Jul. 5, 2016.
Amendment from U.S. Appl. No. 14/565,024 dated Jul. 28, 2016.
Notice of Allowance from U.S. Appl. No. 14/565,024 dated Aug. 30, 2016.
Supplemental European Search Report from European Application No. 02729222.6 dated Aug. 20, 2009.
Response from European Application No. 02729222.6 dated Nov. 17, 2009.
Office Action from European Application No. 0279222.6 dated Sep. 23, 2010.
Response from European Application No. 02729222.6 dated Jan. 28, 2011.
Office Action from European Application No. 02729222.6 dated Sep. 7, 2011.
Response from European Application No. 02729222.6 dated Jan. 10, 2012.
Search Report from European Application No. 05757183.8 dated Oct. 4, 2012.
Office Action from European Application No. 05757183.8 dated Feb. 11, 2013.
Response from European Application No. 05757183.8 dated Aug. 19, 2013.
Search Report from European Application No. 05755966.8 dated Jun. 5, 2012.
Office Action from European Application No. 05755966.8 dated Sep. 27, 2012.
Response from European Application No. 05755966.8 dated Apr. 5, 2013.
Search Report from European Application No. 06112733.8 dated Jan. 12, 2007.
Response from European Application No. 06112733.8 dated Jan. 7, 2009.
Office Action from European Application No. 06112733.8 dated Feb. 19, 2009.
Search Report from European Application No. 12162767.3 dated Dec. 23, 2015.
Extended Search Report from European Application No. 14841802.3 dated Jan. 30, 2017.
Office Action from Japanese Application No. 2007-511105 dated Sep. 3, 2009.
Response from Japanese Application No. 2007-511105 dated Mar. 5, 2010 along with English translation of claims and relevant portion of remarks made in Amendment.
Office Action from Japanese Application No. 2007-515282 dated Jan. 7, 2011.
Response from Japanese Application No. 2007-515282 dated Apr. 7, 2011 along with English translation of claims and relevant portion of remarks made in Amendment.
Office Action from Japanese Application No. 2007-515282 dated Jul. 27, 2011.
Response from Japanese Application No. 2007-515282 dated Mar. 5, 2012 along with relevant portion of remarks made in Amendment.
Office Action from Japanese Application No. 2009-548397 dated Sep. 28, 2012.
Response from Japanese Application No. 2009-548397 dated Mar. 28, 2013 along with English translation of claims and relevant portion of remarks made in Amendment.
Office Action from Japanese Application No. 2010-511374 dated Dec. 28, 2012.
Response from Japanese Application No. 2010-511374 dated Jul. 5, 2013 along with English translation of claims and relevant portion of remarks made in Amendment.
English Translation of Office Action from Japanese Patent Application No. 2016-054033 1 dated May 29, 2018.
Cook Medical brochure pages, Esophageal/Gastric Colonic: Snares, 3 pgs., date is at least as early as Jul. 1, 2013.
Juan-Marie et al. Double-Lumen Snare Injector: Introducing the Double-Lumen Concept in Ancillary Pollypectomy Equipment, Gastrointestinal Endoscopy, vol. 57, No. 5, 2003.
MTW Endoskopie, brochure, one page, date is at least as early as Jul. 1, 2013.
Olympus, EndoTherapy, Polypectomy, brochure, 3 pgs., date is at least as early as Jul. 1, 2013.
English translation of Office Action in Japanese Application No. 2014-004359 dated Jan. 20, 2015.
Extended European Search Report in European Application No. 08756773.1 dated Feb. 23, 2015.
Office Action from U.S. Appl. No. 14/565,024 dated Dec. 9, 2015.
Office Action from European Application No. 05757183.8 dated Nov. 16, 2015.
Response to Office Action from European Application No. 05757183.8 dated Mar. 17, 2016.
Extended European Search Report in European Application No. 08714094.3 dated Jan. 27, 2016.
International Search Report and Written Opinion from PCT/US18/13005 dated Mar. 29, 2018.
Office Action from U.S. Appl. No. 10/146,273 dated Oct. 22, 2003.
Response from U.S. Appl. No. 10/146,273 dated Jan. 16, 2004.
Office Action from U.S. Appl. No. 10/146,273 dated Apr. 14, 2004.
Office Action from U.S. Appl. No. 14/875,028 dated Dec. 26, 2018.
Office Action from U.S. Appl. No. 15/401,545 dated Mar. 8, 2019.
Office Action from U.S. Appl. No. 15/344,915 dated Jan. 18, 2017.
Response Office Action from U.S. Appl. No. 15/344,915 dated Apr. 18, 2017.
Notice of Allowance from U.S. Appl. No. 15/344,915 dated Jun. 26, 2017.
Office Action from U.S. Appl. No. 15/425,228 dated Apr. 12, 2017.
Response to Office Action from U.S. Appl. No. 15/425,228 dated Jul. 10, 2017.
Office Action from U.S. Appl. No. 15/425,228 dated Aug. 23, 2017.
Response to Office Action from U.S. Appl. No. 15/425,228 dated Aug. 31, 2017.
English Translation of Office Action from Japanese Patent Application No. 2016-052687 dated Jan. 31, 2017.
Advanced Line Retrieval Devices Brochure, issued by US Endoscopy 760204, Rev. A, dated at least as early as the filing date of the subject application.
Notice of Allowance from U.S. Appl. No. 15/676,725, dated Feb. 4, 2020.
Notice of Allowance from U.S. Appl. No. 15/401,545, dated Jan. 16, 2020.
Notice of Allowance from U.S. Appl. No. 15/866,401, dated Jan. 23, 2020.
Notice of Allowance from U.S. Appl. No. 15/866,401, dated Mar. 18, 2020.
Response to Office Action from U.S. Appl. No. 15/676,725, dated Jan. 6, 2020.
Response to Office Action from U.S. Appl. No. 14/875,028 dated Jan. 2, 2020.

(56) References Cited

OTHER PUBLICATIONS

Office Action from U.S. Appl. No. 14/875,028 dated Apr. 16, 2020.

* cited by examiner

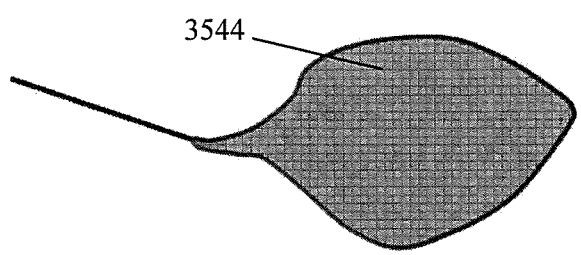
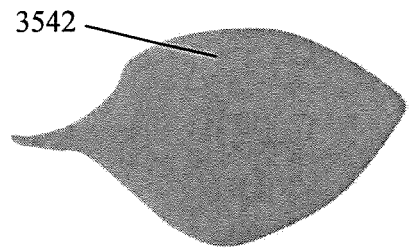
FIG. 11a                FIG. 11b
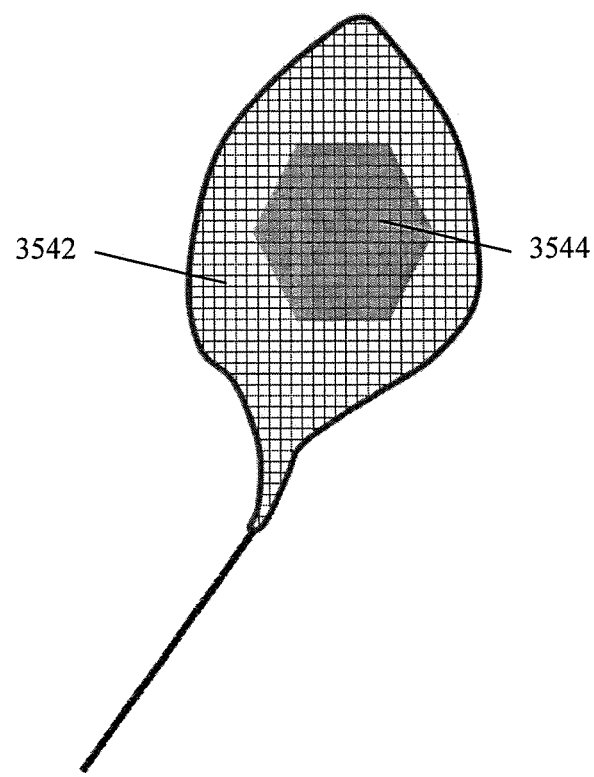
FIG. 12

RETRIEVAL DEVICE

CROSS-REFERENCES

This application claims benefit of U.S. Provisional Patent Application No. 62/444,144, entitled "RETRIEVAL DEVICE," filed on Jan. 9, 2017, the entire disclosure of which is incorporated herein by reference.

TECHNICAL FIELD

The present subject matter is related to an endoscopic retrieval device.

BACKGROUND OF THE INVENTION

Endoscopic retrieval or removal devices are used to recover objects from inside a human subject. Such objects may include excised human tissue, including polyps, foreign objects, or food bolus. Some typical devices include forceps or clasps to grab objects. Certain devices of this type are not well-suited for retrieving heavy, rounded or blunt objects such as large tissue masses, a food bolus, coins, marbles and batteries because the objects are difficult to hold securely. Further, if an object is dropped near the trachea during the removal process, the results can be catastrophic for the patient. Other devices include a variety of net support and net operating structures.

Many retrieval devices are used within an instrument channel of an endoscope during endoscopic medical procedures. These devices are generally expandable and collapsible relative to a tube inserted into the instrument channel. For example, a wire loop at the distal end of the device may expand and collapse relative to the tube by action of a handle at the proximal end of the device. Further, a net may be secured to the expandable and collapsible wire loop.

SUMMARY

One aspect of the present subject matter is to provide a net element with an extra wide tail section. The tail section wraps around the link, the leg portion, or the connection.

Another aspect of the present subject matter is to provide a new weaving pattern. The loop passes through the net element, loops over the edges of the net element, and passes through the net element again from the same face. At least one leg of the loop passes through the tail section at a position at least about 4 mm from a corner defined between the tail section and the loop section of the net element.

Another aspect of the present subject matter is to provide a new shape of the loop. The widest portion of the loop is more proximal to the tubular member than the mid-point of the length of the loop is.

Another aspect of the present subject matter is to provide a net with a combination of net elements, such as combinations of different net geometries and/or different net materials.

Another aspect of the present subject matter is to provide a new and inventive loop. The loop is configured to flex towards only one side. The loop or the net is colored or coded to indicate which side is flexed.

Another aspect of the present subject matter is to provide an improved second end of the tubular member. The second opening of the tubular member is enlarged or flared. Also, the inside surface of the distal portion of the tubular member is smooth and atraumatic to the net.

Another aspect of the present subject matter is to provide a new and inventive arm. The distal ends of two arms are respectively attached to each side of the proximal portion of the loop. The proximal ends of the two arms are attached to the handle. The arms are configured to be pushed towards the distal direction to widen the loop.

BRIEF DESCRIPTION OF THE DRAWINGS

FIGS. 11a and 11b are views of another embodiment of the net;

FIG. 12 is a view of another embodiment of the net;

DETAILED DESCRIPTION

The Detailed Description merely describes preferred embodiments of the invention and is not intended to limit the scope of the invention or claims in any way. Indeed, the invention as described by the claims is broader than and unlimited by the preferred embodiments, and the terms used have their full ordinary meaning.

A device for retrieving an object from within a human subject is disclosed. In discussing the device, the terms distal and proximal are used with respect to the operator's hand. In other words, when the device is used within the instrument channel of an endoscope or similar device, the proximal and distal orientation are relative to the position of the surgeon or operator of the device.

It should also be noted that for the purposes of this application, the terms attach (attached), connect (connected), and link (linked) are not limited to direct attachment, connection, or linking but also include indirect attachment, connection, or linking with intermediate parts, components, or assemblies being located between the two parts being attached, connected, or linked to one another. In addition, the terms attach (attached), connect (connected), and link (linked) may include two parts integrally formed or unitarily constructed.

For exemplary purposes only, the invention will be discussed in regard to a device designed for use within an endoscope for retrieving objects within relatively tight passages, such as for example, impacted food bolus from the esophagus or polyps located within the gastrointestinal tract. It should be apparent to others with ordinary skill in the art that the discussion and Figures included in this application are by way of example only, and that the invention can be utilized with endoscopic retrieval devices having a wide variety of structures, shapes, strengths, or purposes. One of many other exemplary uses for the invention is to remove polyps from the colon.

Several exemplary devices for endoscopic retrieval of an object from within a subject are disclosed in U.S. Pat. No. 5,906,621 to Secrest et al.; U.S. Pat. No. 6,814,739 to Secrest et al.; U.S. Pat. No. 8,016,838 to Secrest et al.; U.S. Pat. No. 8,057,484 to Secrest et al.; U.S. Pat. No. 8,591,521 to Cherry et al.; U.S. Pat. No. 9,204,888 to Cherry et al.; U.S. Pat. No. 9,486,188 to Secrest et al.; U.S. Pat. No. 9,730,716 to Secrest et al.; U.S. Pat. No. 9,826,997 to Cherry et al.; U.S. application Ser. No. 15/676,725 to Secrest et al.; U.S. application Ser. No. 15/875,028 to Cherry et al., each of which incorporated herein by reference in its entirety, to the extent that any do not conflict with the present application.

Figure 1:
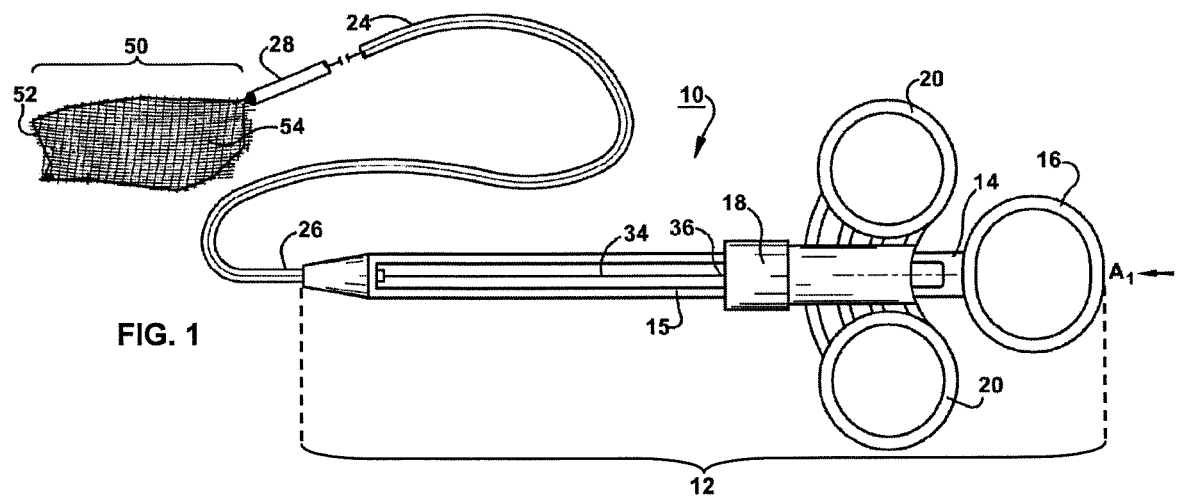
FIG. 1 is a perspective view of a retrieval device constructed in accordance with an embodiment of the present invention.

An endoscopic surgical device 10 for retrieving excised tissue and or foreign bodies from within a subject is illustrated in FIG. 1. The device 10 is so constructed and arranged that it may be inserted into a subject through an orifice or small incision and operated to retrieve a tissue sample previously detached from the subject by a conventional method, e.g., a snare/cautery system. Often, the endoscopic surgical device 10 is delivered via a channel located in and through an endoscope.

The device 10 can be used with any suitable or conventional endoscopic or laparascopic surgical equipment. For purposes of this disclosure the device 10 is described in the context of use with an endoscope/colonoscope/sigmoidoscope type apparatus (not illustrated), of conventional or suitable construction. The scope is provided with an elongated body having a controllably flexible projecting end region. Surgical instruments, such as the device 10, may be introduced through an instrument channel, which extends through the scope body, for retrieving tissue targeted by the surgeon manipulating the scope.

FIG. 1 is a perspective view of a retrieval device 10 constructed in accordance with an embodiment of the present subject matter. The device 10 includes an actuating body 12 attached to a motion transmitting link 34 at a proximal end 36 of the motion transmitting link 34. By affecting the motion transmitting link 34, the actuating body 12 can transmit considerable deployment and retractive forces to a net 50 while enabling an endoscope body to be freely manipulated and flexed to position the net where desired. In other embodiments, the actuating body 12 can be any number of actuating devices or handles recognized by one of ordinary skill in the art.

In the particular embodiment shown in FIG. 1, the actuating body 12 includes a support base 14. The support base 14 includes a ring 16 at a proximal end. The actuating body 12 also includes a handle 18 having two rings 20. The handle 18 is mounted over an interior section 15 of the support base 14 and is movable relative to the support base in the direction A1 as illustrated, or in an opposing direction. For example, an operator may place a finger in each of the rings 20 and thumb of the same hand in the support base ring 16. By moving the two fingers in the direction A1, an operator can move the handle 18 relative to the support base 14. In contrast, the handle 18 can be slid in a direction opposite A1 by pulling one's fingers towards one's thumb.

The device 10 can also include an elongated introducer member or tubular member 24 having a first end 26 fixed to the support base 14 and a second end remote from the actuating body. The tubular member 24 and the support base 14 of the present embodiment are a fixed support assembly for the moving parts of the device 10. The tubular member 24 may be any suitable, small-diameter tube formed of a non-reactive low-friction flexible material, such as for example, polytetrafluorethylene. The tubular member 24 defines a lumen with an opening at the tubular member second end.

In the embodiment of FIG. 1, the motion transmitting link 34 is connected to the actuating body 12 via handle 18. The link can be a solid cable, a hollow tube, or any suitable elongated object or combination of objects for transferring axial motion and considerable deployment and retractive forces from the handle 18 to other parts of the device. The link 34 has first end 36 fixed to the handle 18 and a second end remote from the actuating body portion 12, connecting to retrieval net 50 via connection 28. The link extends substantially through the tubular member 24 lumen. The link may be constructed of any suitable rigid or semi-rigid material. The link may be one piece or formed from a series of pieces and connections, such as for example, hypodermic tubes, swage connections, and cables. In some embodiments, the link 34 is rotatable by the actuating body 18 having a rotation function. A rotatable link 34 is made of nitinol wire or other suitable wire. In some other embodiments, the rotatable link 34 has torque tube filar construction.

Still referring to FIG. 1, the device also includes a retrieval net 50. The retrieval net 50 is used by the operator to capture and retrieve objects from within a human subject. The retrieval net 50 includes a loop 52, or loop portion, and at least one net element 54 secured to the loop. The at least one net element 54 may be supported by the loop 52 by threading or weaving the loop through holes in the at least one net element. It may also be supported by sewing or otherwise attaching the net element to the loop through use of a thread or other sewed lines. However, the at least one net element 54 may be supported by the loop 52 by any suitable method known in the art, such as welding, melding, or gluing. Further, it should be apparent to others with ordinary skill in the art that a variety of net shapes and sizes can be utilized in the practice of this invention. Additional, inventive net and loop arrangements are described herein.

Figure 2:
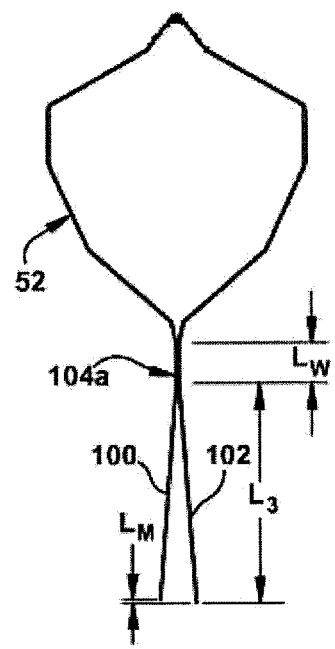
FIG. 2 is a view of a portion of the device of FIG. 1, showing the loop.
Figure 3A:
FIGS. 3a-3d are views of a portion of the device of FIG. 1, showing the loop and the net elements.
Figure 3B:
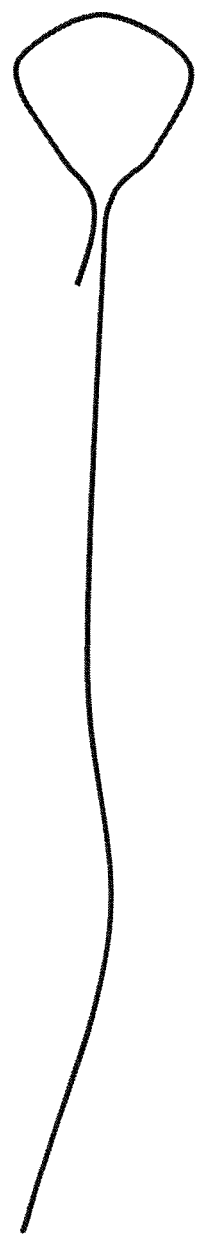
Figure 3C:
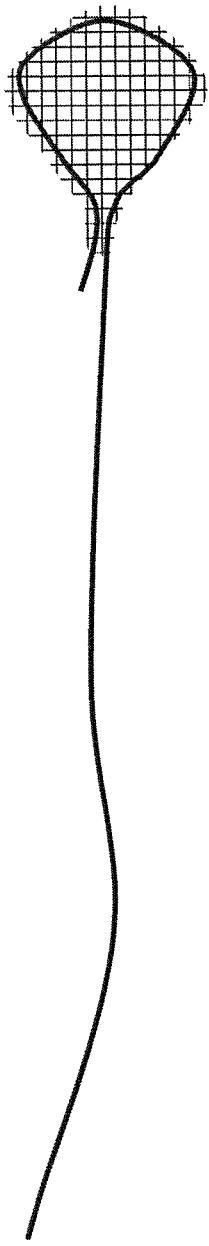
Figure 3D:
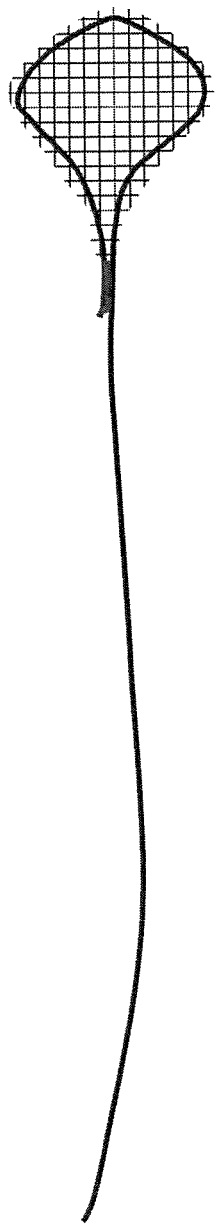

Referring now to FIG. 2, the loop 52 of the device of FIG. 1 is shown. The loop 52 is shown in FIG. 2 in a polygon form prior to assembly within the tubular member 24. The wire of the loop 52 extends back toward the proximal end of the device 10 and forms two adjacent, or leg, portions 100 and 102. The leg portions 100, 102 are secured to each other by a connection 104 a, such as for example, with a weld or by crimping or twisting the portions together, having an axial length Lw of sufficient size to secure the portions together. As shown, the leg portions 100, 102 are joined by a weld 104a. The leg portions 100, 102 extend beyond the weld 104a a length L3. The extension lengths of the two leg portions 100, 102 may be mismatched by a length Lm, but this mismatch is not required. The mismatch in extension lengths of the two leg portions 100, 102 allows space to connect the two leg portions to the link 34 through the connection 28 during manufacturing of the device.

Referring to FIG. 1, the connection 28 connects the second, distal end of the link 34 to retrieval net 50. The connection 28 may be a weld between the link 34 and the loop 52 or any means capable of attaching link 34 and the retrieval net 50 recognized by one of ordinary skill in the art, including adhesive or a threaded connection between the link 34 and the loop 52. The connection 28 may also be a junction between at least one net element 54 and link 34.

Figure 4A:
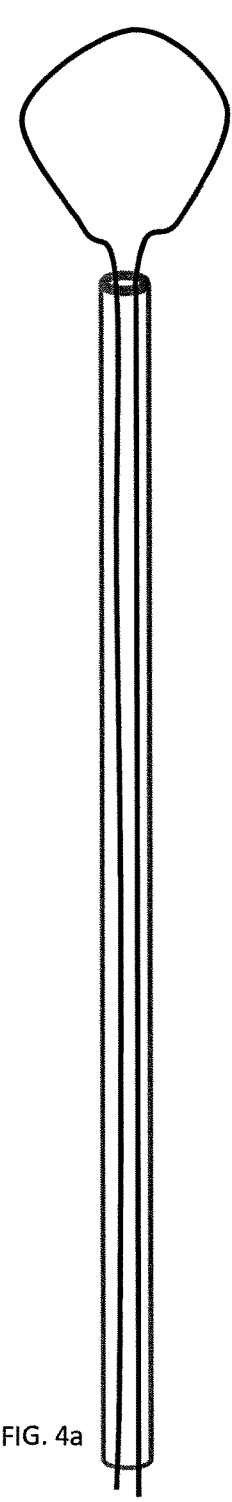
FIGS. 4a-4d are views of a portion of the device of FIG. 1, showing the loop, the net elements, and the tubular member.
Figure 4B:
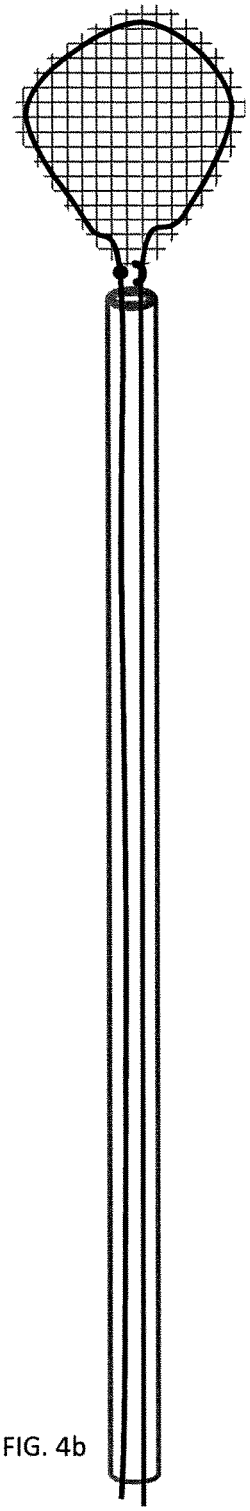
Figure 4C:
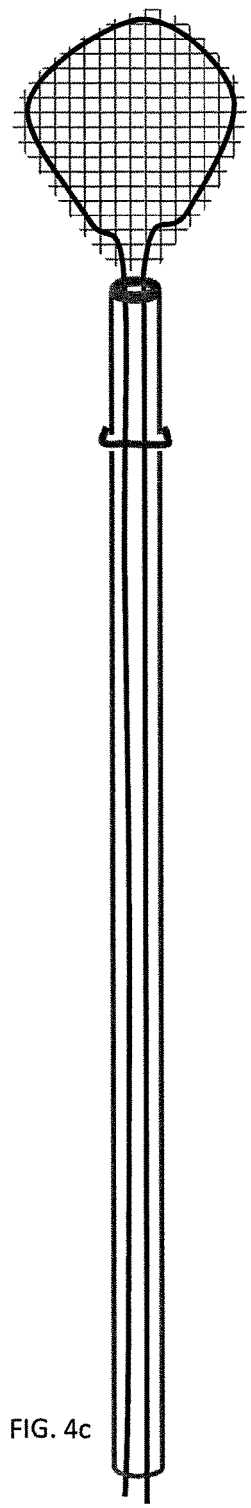
Figure 4D:
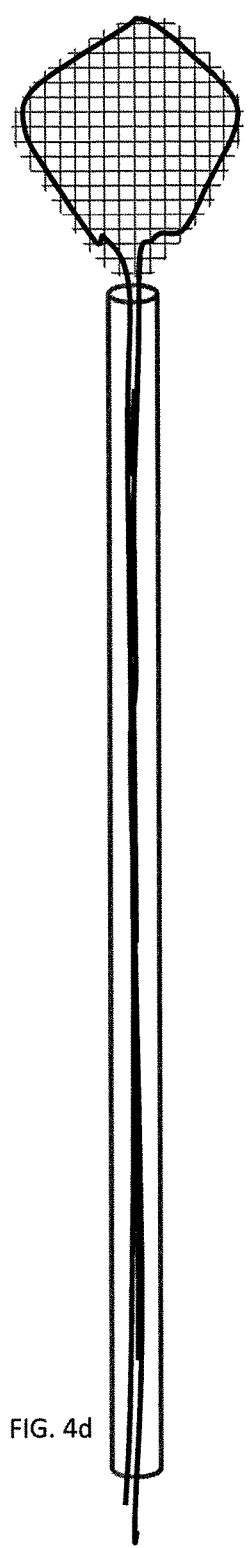

One of ordinary skill in the art should realize that the link 34, the connection 28, and the loop 52 could be formed by one wire. In the embodiments in FIG. 3a-3d, a single wire forms both the loop 52, the connection 28, and the link 34. The wire comprises a short leg and a long leg. The short leg welds, crimps, or otherwise bonds to the long leg and forms the loop. The wire may be made of nitinol or other suitable material. In the embodiments in FIG. 4a-4d, the single wire has two long legs. Both legs pass through the tubular member. One or more stops are configured to be tied, welded, crimped, or otherwise bonded to at least one leg. In such, the stops limit net migration. In some embodiments shown as FIG. 4b, one or more stops are added to the tubular member, and may be tied, welded or glued. The stops could be two "balls" or other features larger than net openings, or be a ball and socket that would help maintain the positional relationship of the wires as the net was retracted. Position could be a locking mechanism or merely passive positioning. FIG. 4c shows that the tubular member may comprise stops, such as a notch and an O-ring. One of ordinary skill in the art should understand that any modifications or structures on the tubular member, such as a crimp, glue or taper to decrease the inner diameter of the tubular member could be used to restrict the movement of net. In both instances, a tie or attachment may be needed. Such a tie or attachment is the most effective at the distal end. This would also help center the wires and net in the tubular member. In the embodiments of FIG. 4d, the two wire legs are welded, glued or crimped together, either a couple places or over the length, to give the legs rigidity.

As discussed, the retrieval net 50 is designed for resilient movement between two positions. FIG. 1 shows the retrieval net 50 in a deployed position. The retrieval net 50 can also be disposed within the tube 24 for deployment and retrieval through the tubular member lumen opening. By movement of the handle 18 relative to the body 14, the retrieval net 50 is movable between either the deployed or stored positions.

Figure 5:
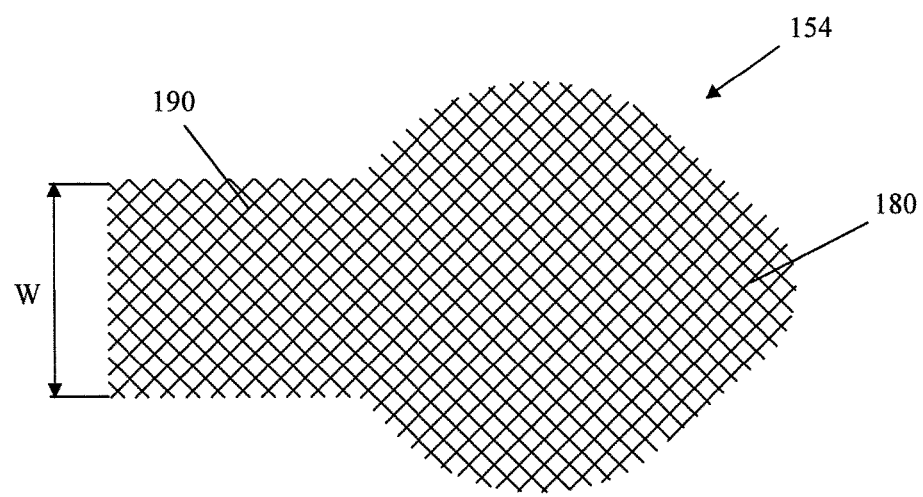
FIG. 5 is a view of an embodiment of the net element.

One aspect of the present subject matter is to provide a net element with an extra wide tail section. Referring to FIG. 5, the net element 154 comprises a loop section 180 and a tail section 190. The width W of the tail section 190 is about 10 mm-35 mm. In some embodiments, the width W of the tail section 190 is about 25 mm.

Figure 6:
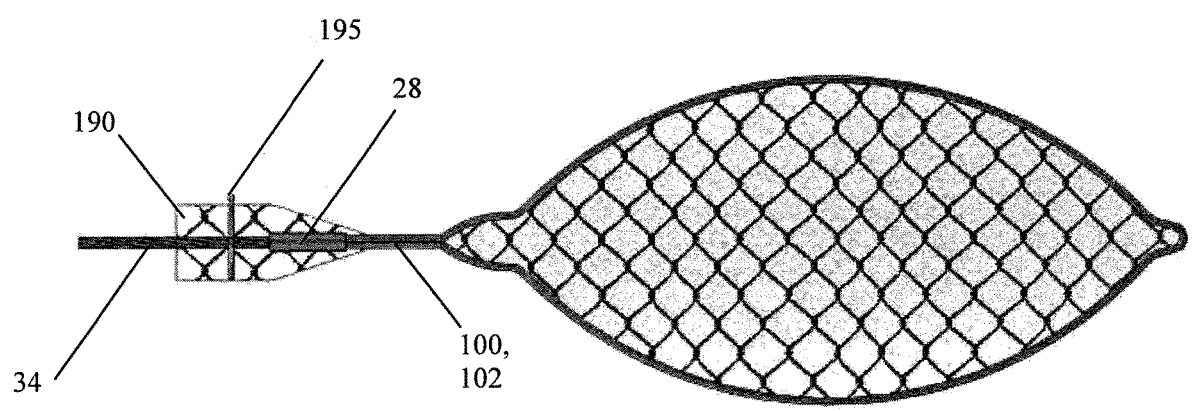
FIG. 6 is a view of an embodiment of the net.

In some embodiments of FIG. 6, the tail section 190 was wrapped around the link 34 by tying a tether 195. In other embodiments, the tail section 190 wraps around at least one of the leg portions 100, 102. In other embodiments, the tail section 190 wraps around the connection 28. One of ordinary skill in the art should understand that the tail section is not necessarily tied by the tether 195, and could be welded or glued. The wider tail section 190 helps to prevent over stretching the proximal end of the net created by the net element when retrieving an object and thus reduces the chance of tearing the mesh. It also aides in packing the mesh into the tubular member 24.

Figure 7A:
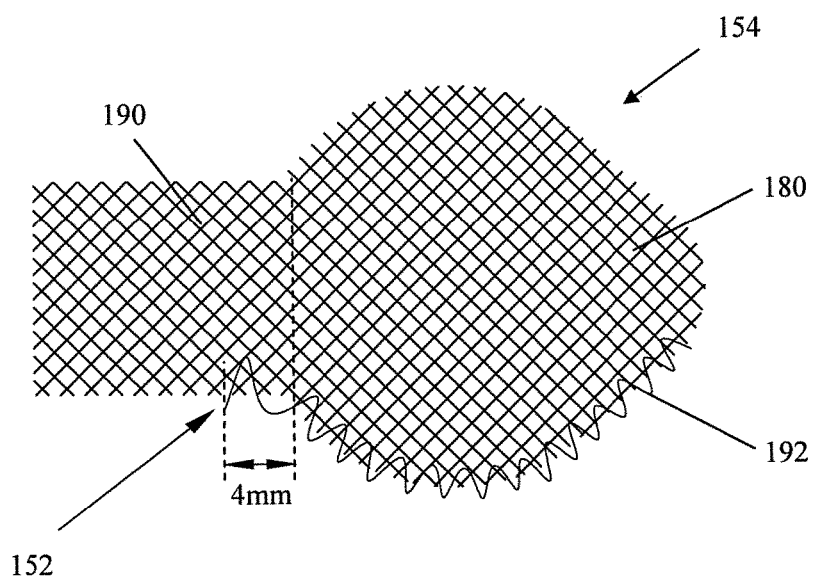
FIGS. 7a and 7b is views of an embodiment of the net weaving pattern.
Figure 7B:
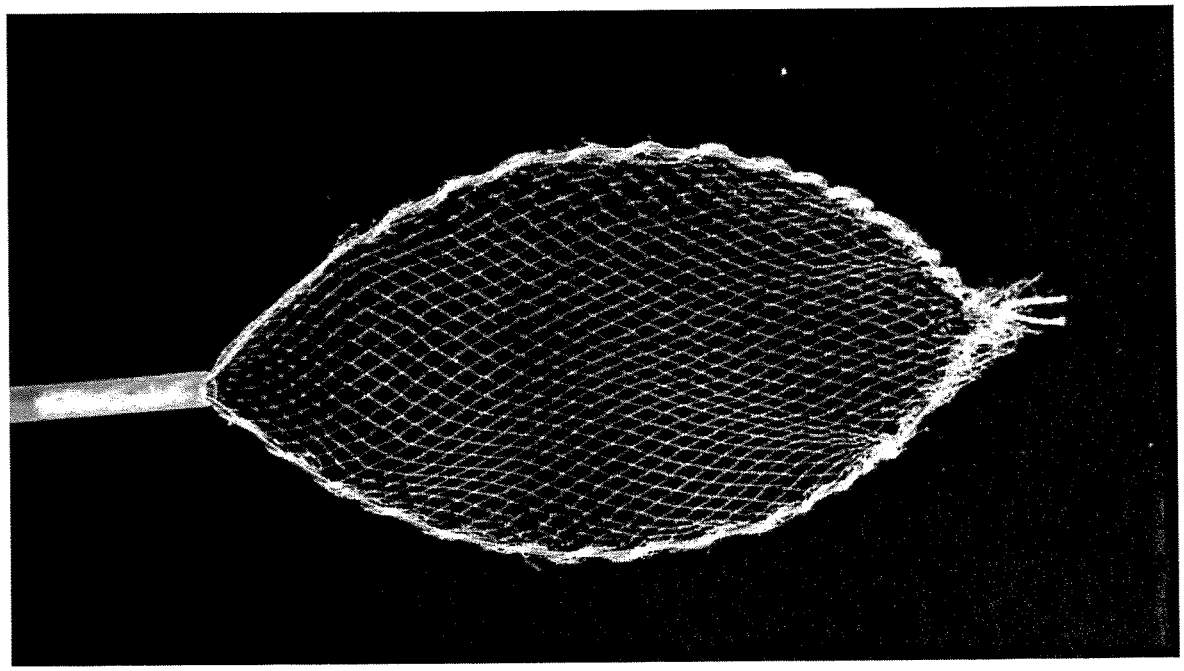

Another aspect of the present subject matter is to provide a new weaving pattern. Referring to FIG. 7a, in some embodiments, the loop 152 passes through the net element 154, loops over the edges of the net element 154, and passes through the net element 154 again from the same face. The loop 152 weaves following a direction 192. FIG. 7b shows a net having such a weaving pattern. Such weaving pattern helps with visualization while using the device.

In some embodiments, the loop 152 passes through the tail section 190. In some embodiments, one leg of the loop 152 passes through the tail section 190. In some other embodiments, both legs of the loop 152 pass through the tail section 190. In some other embodiments, at least one leg of the loop 152 passes through the tail section 190 at a position between about 1 mm to 6 mm from a corner defined between the tail section 190 and the loop section 180 of the net element 154. In some other embodiments, at least one leg of the loop 152 passes through the tail section 190 at a position between about 2 mm to 5 mm from a corner defined between the tail section 190 and the loop section 180 of the net element 154. In some embodiments, at least one leg of the loop 152 passes through the tail section 190 at a position at least about 4 mm from a corner defined between the tail section 190 and the loop section 180 of the net element 154. In some other embodiments, both legs of the loop 152 pass through the tail section 190 at a position between about 1 mm to 6 mm from a corner defined between the tail section 190 and the loop section 180 of the net element 154. In some other embodiments, both legs of the loop 152 pass through the tail section 190 at a position between about 2 mm to 5 mm from a corner defined between the tail section 190 and the loop section 180 of the net element 154. In some embodiments, both legs of the loop 152 pass through the tail section 190 at a position at least about 4 mm from a corner defined between the tail section 190 and the loop section 180 of the net element 154. In such, the weaving pattern helps to reduce wear of the net element when retracting the net into the tubular member.

Figure 8:
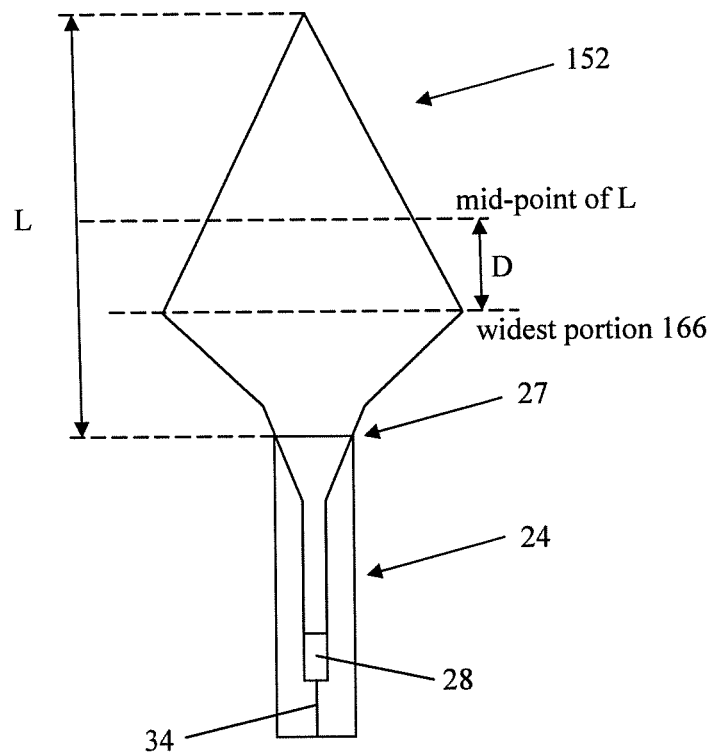
FIG. 8 is a view of an embodiment of the loop.

Another aspect of the present subject matter is to provide a new shape of the loop. Referring to FIG. 8, in some embodiments, the loop 152 comprises a widest portion 166 and a length L measured between a proximal end and a distal end. The proximal end is defined where the loop begins to close during retraction into the tubular member, irrespective of where the loop connection physically may occur. The distal end is defined by the most distal end, or ends, of the loop 152. In any instance where there are proximal legs that are excessively long, and/or the distal tip is inverted or of any other unusual geometry, the midpoint shall be considered only with respect to the broad portions of the form, which is defined between the proximal end and the distal end(s). The widest portion 166 of the loop 152 is more proximal to the tubular member 24 than the mid-point of the length L of the loop 152 is. In other words, the widest portion 166 is closer to the tubular member 24 than the mid-point of the length L of the loop 152, such that the loop 152 is easier to be controlled during the procedures. In some embodiments, the distance D from the mid-point of the length L of the loop 152 to the widest portion 166 of the loop 152 is about 3%-45% of the length L. In some embodiments, the distance D from the mid-point of the length L of the loop 152 to the widest portion 166 of the loop 152 is about 10%-35% of the length L. In some embodiments, the distance D from the mid-point of the length L of the loop 152 to the widest portion 166 of the loop 152 is about 12%-25% of the length L.

Another aspect of the present subject matter is to provide a net with a combination of net elements, such as combinations of different net geometries and/or different net materials. Such a net provides better support and strength that otherwise could not be achieved by a single net geometry/material.

The net comprises at least a first net element and a second net element, respectively, having different geometry or material properties. The property differences may be caused by different alignments of multiple nets or multiple net pieces, weave densities, geometries, materials, or any combination of the above properties. For example, in some embodiments, the first and second net elements have different alignments or zones. In some embodiments, the first and second net elements have different weave densities. In some embodiments, the first and second net elements use different materials. In some embodiments, the first and second net elements have different geometries. As a result of an embodiment, the first net element is more elastic, while the second net element has more strength or resiliency.

Individual net element may, but not necessarily, fully cover the loop. In some embodiments, the first and second net elements respectively cover the whole loop. In some embodiments, one of the first and second net elements fully covers the loop; and another net element covers only a part of the loop. In some embodiments, none of the first and second net elements covers the whole loop. However, the first and second net elements connect each other to cover the whole loop.

Figure 9A:
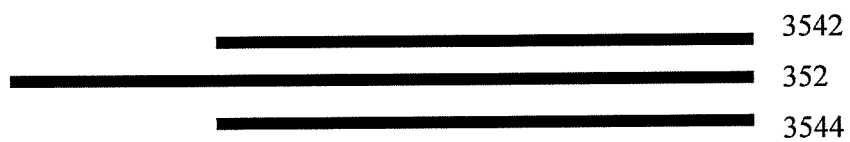
FIGS. 9a-9c are side views of unassembled loops and net elements.
Figure 9B:
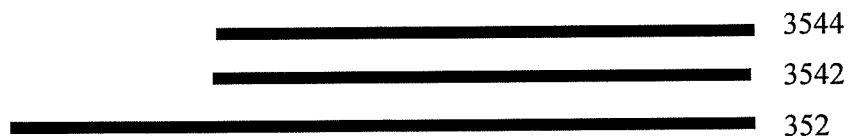
Figure 9C:
Figure 10A:
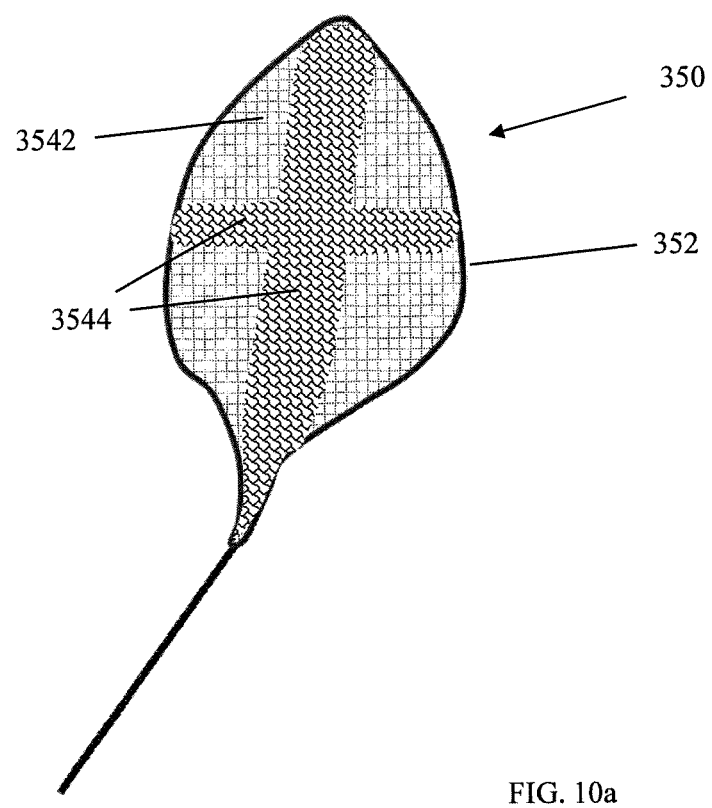
FIGS. 10a-10f are views of embodiments of the net.
Figure 10B:
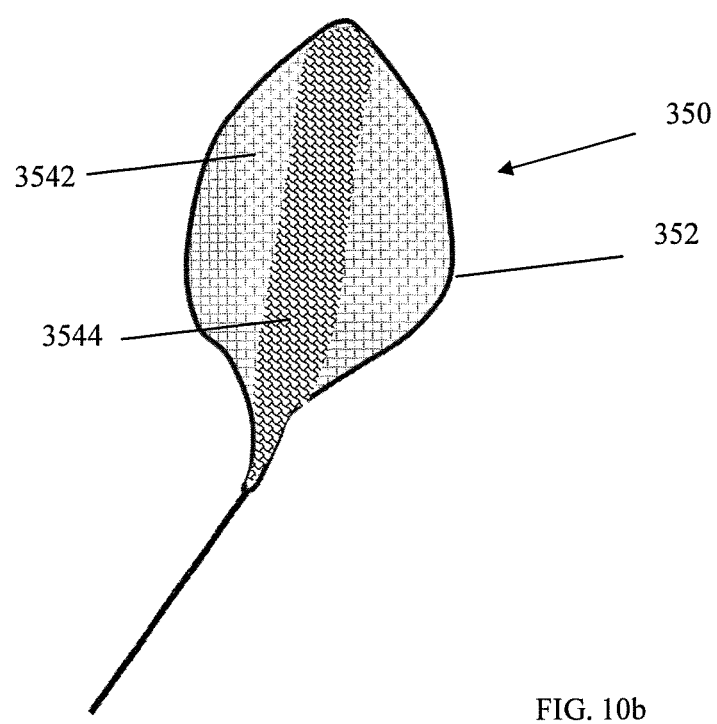
Figure 10C:
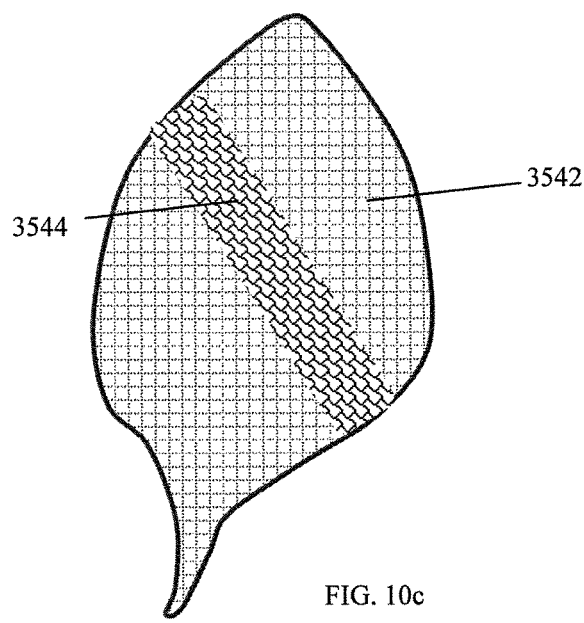
Figure 10D:
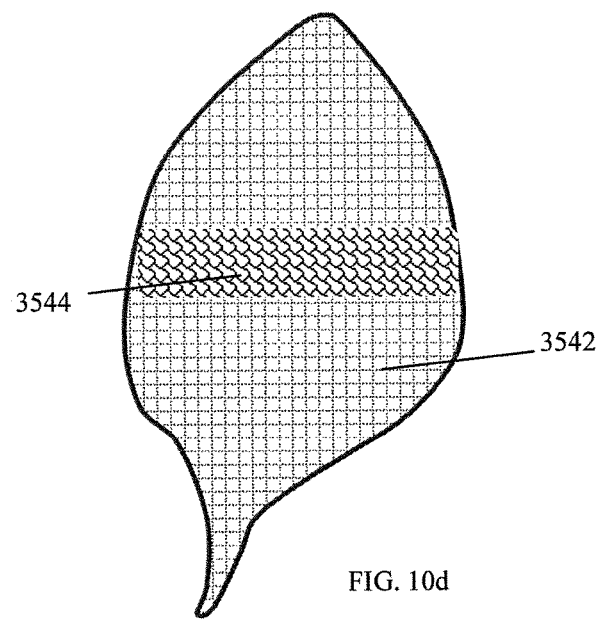
Figure 10E:
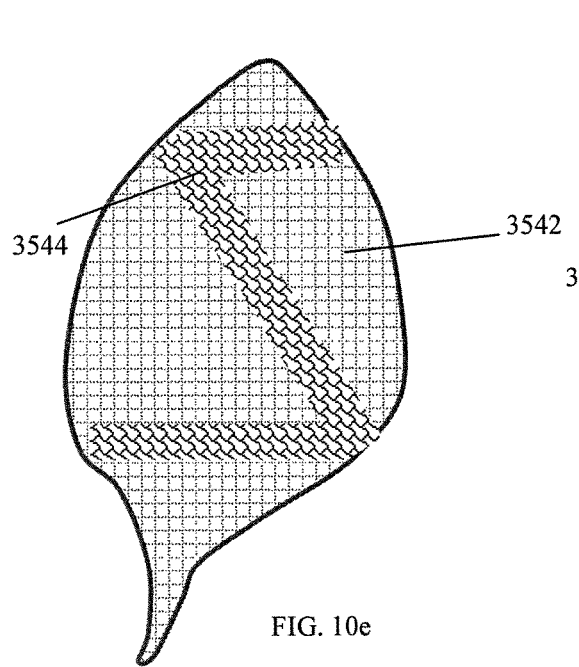
Figure 10F:
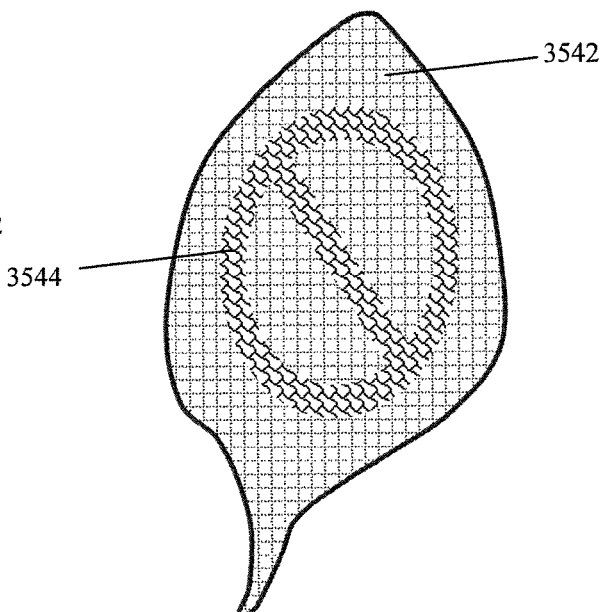

Referring to FIGS. 9a-9c, in some embodiments shown in FIG. 9a, the first net element is attached to one side of the loop, while the second net is attached to another side of the loop. In some embodiments shown in FIG. 9b, the first and second nets are attached to the same side of the loop. In some embodiments shown in FIG. 9c, the first net element is attached to one side of the loop; and the second net element is attached the first net element, or vice versa. A person skilled may readily understand that the net element could be weld, glued, or otherwise attached by a known mechanism to the loop. Similarly, the second net element could be weld, glued, or otherwise attached by a known mechanism to the first net element.

A person skilled in the art should readily understand that the net elements discussed above could also include plastic film or plastic membrane, such as Tyvek, or a known material.

In the embodiments of FIGS. 10a-10f, the net 350 comprises the first and second net elements 3542, 3544. The first net element 3542 fully covers the loop 352. The second net element 3544 covers only a portion of the loop. The second net elements in FIGS. 10a-10f have various shapes but both provide a better supporting function than a single net element. The first and second net elements 3542, 3544 have different weave patterns. The first and second net elements 3542, 3544 are also made by different materials. The first and second net elements 3542, 3544 work synergistically to provide the best performing net that will still pack into the tubular member 24. It should be noted that these combination net geometries could be woven with the appropriate configuration, had the net geometry welded and/or bonded to create it, or even welded or otherwise bonded in a layered approach while on the loop. It is also possible that one skilled in the art could merely weave or attach the secondary weave configuration in place without them being bonded to each other. This would allow some independent motion, but still produce positive synergistic effects. It should be further noted that it is possible to create these asymmetrical net configurations by a secondary weaving or threading of fibers within or adjacent to the substrate net in a parallel, perpendicular or other geometric pattern with respect to the loop, not unlike, but not limited to, those shown in FIGS. 10a to 10f.

Figure 13:
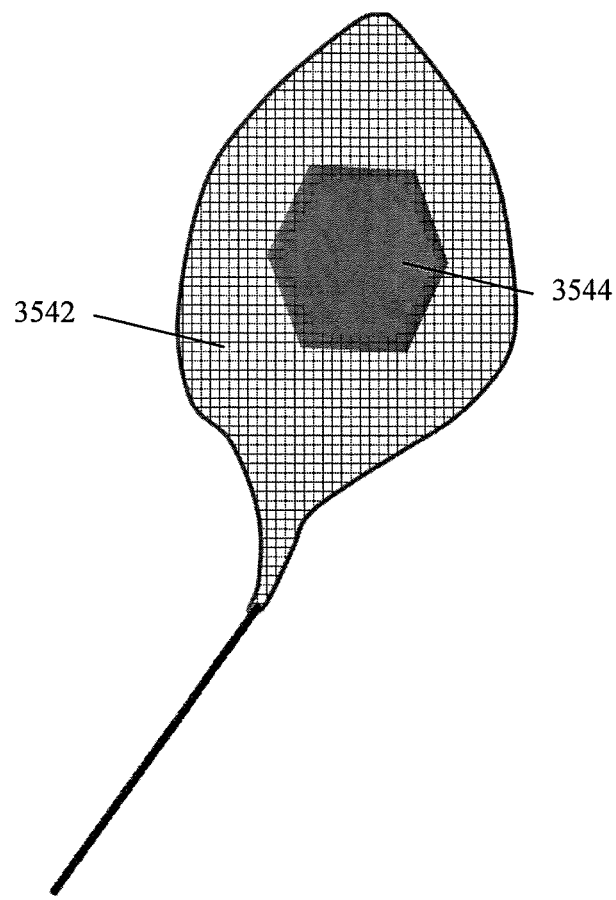
FIG. 13 is a view of another embodiment of the net.

In the embodiment of FIGS. 11a and 11b, both the first and second net elements 3542, 3544 fully covers the loop. In the embodiment of FIG. 12, the first net element 3542 is made of woven or knitted material. The second net element 3544 is made of plastic film. The first net element 3542 fully covers the loop. The second net element 3544 is attached the middle portion of the first net element 3542 to add support and strength. In the embodiment of FIG. 13, the middle portion of the first net element 3542 is removed and is replaced with the second net element 3544. A person skilled in the art will also realize that the second net element could also be a woven or knitted material instead of plastic film. Also, the first net element could be plastic film instead of a woven or knitted material. Furthermore, it should be apparent that the second element can be woven, sewn, or welded onto the first net element.

Figure 14A:
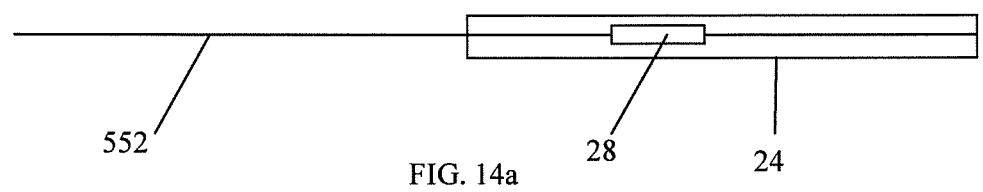
FIGS. 14a and 14b are views of another embodiment of the loop.
Figure 14B:
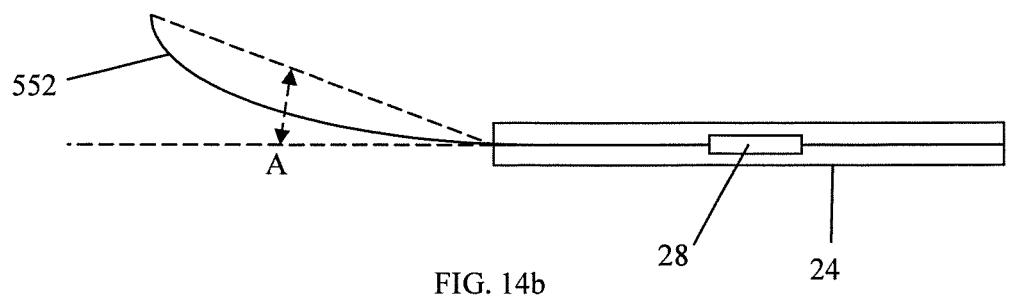
Figure 15A:
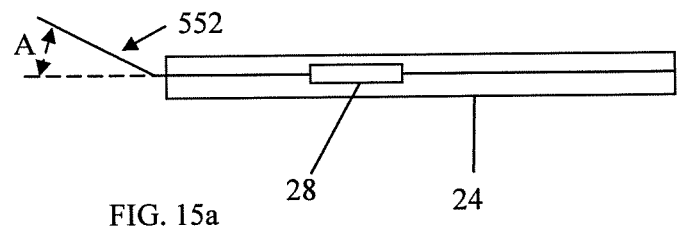
FIGS. 15a and 15b are views of another embodiment of the loop.
Figure 15B:
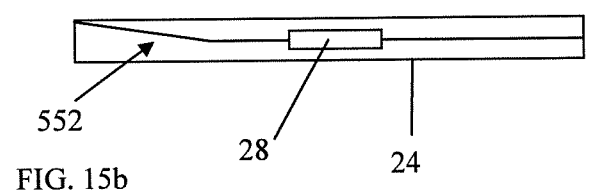

Another aspect of the present subject matter is to provide a new and inventive loop. Referring to FIGS. 14a and 14b, because of its shape memory nature, the loop 552 is so constructed that the loop 552 remains in a substantial level plane at its deployed position; while the loop 552 substantially flexes towards only one direction when the loop 552 is actuated from its deployed position towards its stored position. Person skilled in the art could understand that the loop 552 flexes towards one direction when the loop 552 is at its deployed position. In some embodiment, the loop flexes in a curved fashion. In some other embodiments in FIGS. 15a and 15b, the loop 552 with at least one memory bend flexes towards one direction when the loop 552 is at its deployed position. In some embodiments in FIGS. 14a, 14b, 15a, and 15b, the loop 552 is configured to flex at an angle A of about 20 to 60 degrees. In some other embodiments in FIGS. 14a, 14b, 15a, and 15b, the loop 552 is configured to flex at an angle A of about 30 to 35 degrees.

In some embodiments, the loop 552 is rotatable with the rotatable link and the rotatable actuating body 18 described above. Depending on the position of the object retrieved, the loop 552 could rotate to a desired angle to flex up or down to achieve a desired result. In some embodiments, the loop 552 or the net is colored or coded at certain areas to remind the operator that which direction the loop 552 flexes. In one embodiment, at least part of the loop 552 is made of memory materials, such as nitinol or other suitable wire.

Figure 16A:
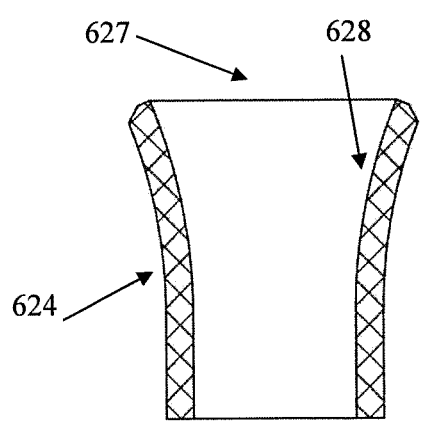
FIGS. 16a and 16b are views of embodiments of the tubular member.
Figure 16B:
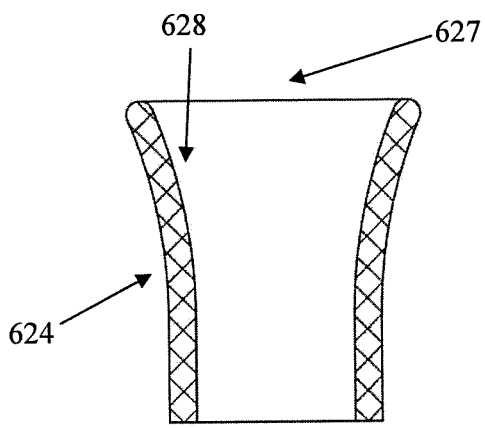

Another aspect of the present subject matter is to provide an improved second end of the tubular member. Referring to FIGS. 16a and 16b, in some embodiments, the second end 627 of the tubular member 624 is enlarged. In some embodiments, the second end 627 of the tubular member 624 is flared. This aides in packing the net element into the tubular member during the retraction.

In some embodiments, the inside surface 628 of the distal portion of the tubular member 624 is smooth and atraumatic. In some embodiments, the second end 627 of the tubular member 624 is an atraumatic tip. This helps to reduce the chances of the net elements from catching or tearing on the distal opening of the tubular member during the retraction. In some embodiments, the outside surface of the distal portion of the tubular member 624 is smooth and atraumatic.

Another aspect of the present subject matter is to provide a new and inventive arm. The device further comprises at least one arm. The arm has a distal end and a proximal end. The distal end is securely attached to the loop. In some embodiments, the distal end is securely attached to the proximal portion of the loop. A person skilled in the art could understand that the attachment could be welding, gluing, tying, or otherwise known attachment mechanisms.

Figure 17A:
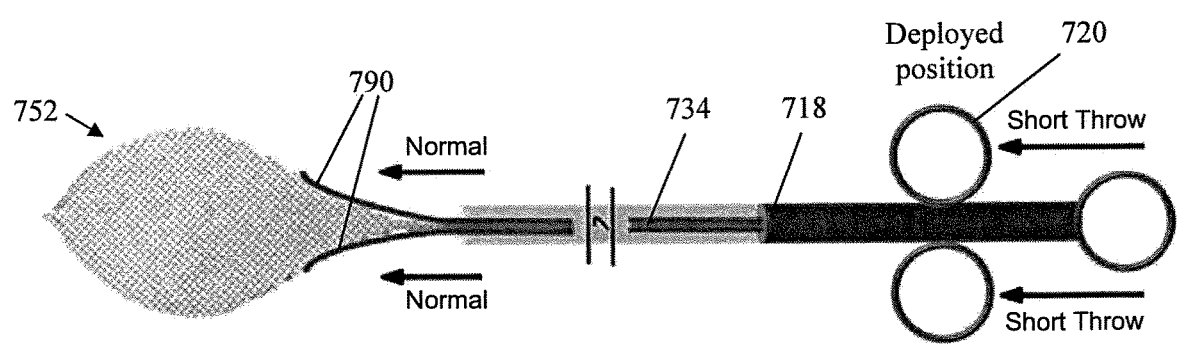
FIGS. 17a and 17b are views of an embodiment of an arm.
Figure 17B:
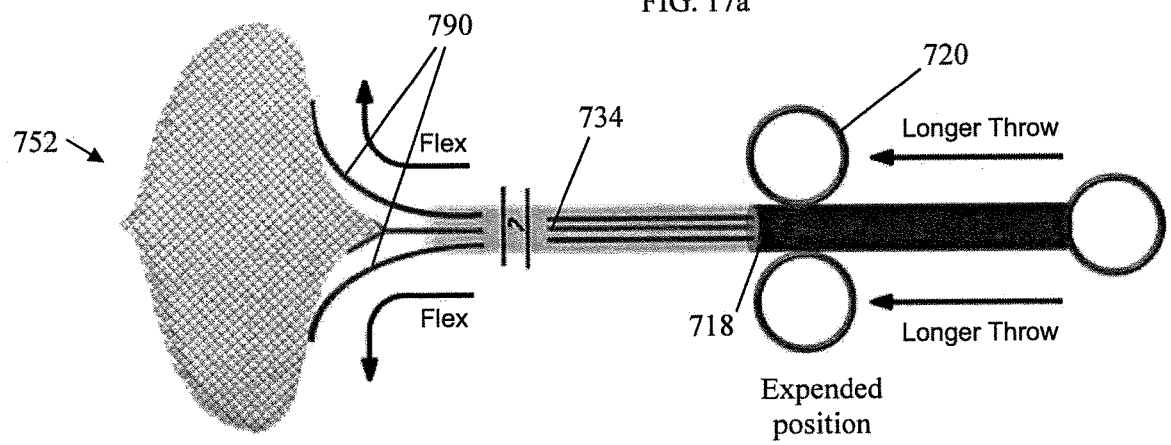

In some embodiments in FIGS. 17a and 17b, the device comprises two arms 790. The distal end of each of the arms 790 is securely attached to the proximal portion of the loop 752. The proximal end of each of the arms 790 is attached to the handle 718. The link 734 is shorter than the arms 790 and has a dead stop (not shown) in the handle 718. When the finger ring 720 is actuated about ½ way, the link 734 and the arms 790 move together to push the loop to its deployed position. As such, the net has a pouch volume and capacity. When the finger ring 720 is actuated further than about ½ way, the link 734 is fixed and the arms 790 are allowed to push out further. The arms 790 force the loop 752 to an expended position. As such, the loop 752 flexes perpendicular to the axis of the tubular member. This causes the net element to stretch tight like a tennis racket. This could help in removal of polyps and/or food debris and also could help scoop and/or move items into a better capture position.

A person skilled in the art should understand that the endoscopic device described in the present subject matter is not necessary to comprise the support assembly (including the base and the elongated tubular member) and/or the transmitting assembly (including the handle and the link). A handle may be formed by or connected to the proximal end of the loop.

While several embodiments of the invention have been illustrated and described in considerable detail, the present invention is not to be considered limited to the precise construction disclosed. Various adaptations, modifications and uses of the invention may occur to those skilled in the arts to which the invention relates. It is the intention to cover all such adaptations, modifications and uses falling within the scope or spirit of the claims filed herewith.

What is claimed is:

1. An endoscopic device for retrieving an object from within a human body, the device comprising:
    a transmitting assembly comprising: a handle; and a link having a first end attached to the handle and a second end,
    a wire defining a loop portion and at least one leg portion, wherein the at least one leg portion is disposed proximal from the loop portion and a proximal end of the at least one leg portion is secured to the second end of the link,
    a net element having a loop section secured to the loop portion,
    wherein the loop portion is movable between an expanded position and a collapsed position by action of the handle,
    wherein a widest portion of the loop portion is more proximal to a proximal end of the loop portion than a mid-point of a length of the loop portion is, at least one arm attached to a proximal portion of the loop portion; wherein a proximal end of the at least one arm is attached to the handle at a proximal end of the device, wherein the at least one arm is configured to be articulated in a manner to widen or narrow the loop portion.

2. The endoscopic device of claim 1, wherein a distance from the mid-point of the length of the loop portion to the widest portion of the loop portion is about 3%-45% of the length.

3. The endoscopic device of claim 2, wherein the distance from the mid-point of the length of the loop portion to the widest portion of the loop portion is about 10%-35% of the length.

4. The endoscopic device of claim 3, wherein the distance from the mid-point of the length of the loop portion to the widest portion of the loop portion is about 12%-25% of the length.

5. The endoscopic device of claim 1, wherein the net element further comprises a tail section secured to the link.

6. The endoscopic device of claim 5, wherein the tail section is secured to the link by a tether.

7. The endoscopic device of claim 5, wherein the tail section is glued to the link.

8. The endoscopic device of claim 5, wherein the tail section has a width of 10-25 mm.

9. The endoscopic device of claim 5, wherein the loop portion passes through the net element, loops over the edges of the net element, and passes through the net element again from the same face.

10. The endoscopic device of claim 5 further comprising a plurality of the following patterns: the loop portion passing through the net element, looping over the edges of the net element, and passing through the net element again from the same face.

11. The endoscopic device of claim 5, wherein at least one leg portion passes through the tail section at a position between about 1 mm to 6 mm from a corner defined between the tail section and the loop section of the net element.

12. The endoscopic device of claim 11, wherein the at least one leg portion comprises two leg portions, both leg portions pass through the tail section at a position between about 1 mm to 6 mm from the corner.

13. The endoscopic device of claim 11, wherein at least one leg portion passes through the tail section at a position between about 2 mm to 5 mm from the corner.

14. The endoscopic device of claim 13, wherein the at least one leg portion comprises two leg portions, both leg portions pass through the tail section at a position between about 2 mm to 5 mm from the corner.

15. The endoscopic device of claim 5, wherein at least one leg portion passes through the tail section at a position at least about 4 mm from a corner defined between the tail section and the loop section of the net element.

16. The endoscopic device of claim 15, wherein the at least one leg portion comprises two leg portions, both leg portions pass through the tail section at a position at least 2 mm from the corner.

17. The endoscopic device of claim 1, wherein the net element comprises combinations of different net geometries and/or different net materials.

18. The endoscopic device of claim 1, wherein the loop portion is configured to flex towards only one side.

19. The endoscopic device of claim 1, wherein the loop portion or the net element is colored or coded or positionally identified.

20. The endoscopic device of claim 1, further comprising: a support assembly comprising a base and an elongated tubular member, wherein the handle is movable relative to the base, and the link extends through at least a portion of the tubular member.

21. The endoscopic device of claim 20, wherein a distal opening of the tubular member is enlarged or flared.

22. The endoscopic device of claim 20, wherein an inside surface of the distal portion of the tubular member is smooth and atraumatic.

23. The endoscopic device of claim 20, wherein an outside surface of the distal portion of the tubular member is smooth and atraumatic.

* * * * *